(12) United States Patent
Cook et al.

(10) Patent No.: US 11,291,181 B2
(45) Date of Patent: Apr. 5, 2022

(54) PEPPER CULTIVAR RPP 46475 HAVING RESISTANCE TO BACTERIAL LEAF SPOT

(71) Applicant: Syngenta Crop Protection AG, Basel (CH)

(72) Inventors: Kevin Cook, Naples, FL (US); Laure Didierlaurent, Beaumes de Venise (FR); Sayed Z. Islam, Naples, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 16/884,881

(22) Filed: May 27, 2020

(65) Prior Publication Data

US 2021/0368728 A1 Dec. 2, 2021

(51) Int. Cl.
*A01H 1/00* (2006.01)
*A01H 5/08* (2018.01)
*A01H 6/82* (2018.01)

(52) U.S. Cl.
CPC ............... *A01H 6/822* (2018.05); *A01H 5/08* (2013.01)

(58) Field of Classification Search
None
See application file for complete search history.

(56) References Cited

U.S. PATENT DOCUMENTS

2018/0007855 A1\* 1/2018 Just ..................... A01H 5/08

OTHER PUBLICATIONS

Larkin et al., Theor. Appl. Genet., vol. 60, 1981, pp. 197-214.\*
Page from Syngenta Flowers North America Catalog "Bayonet" variety page, "https://www.syngentaflowers-us.com/product/garden_vegetable/70024336", (2020).
Vallejos et al., "Characterization of two recessive genes controlling resistance to all races of bacterial spot in peppers," Theor Appl. Genet (2010); 121: 37-46.

\* cited by examiner

*Primary Examiner* — Phuong T Bui
(74) *Attorney, Agent, or Firm* — Amanda W. Bublitz

(57) ABSTRACT

The present invention provides pepper plant RPP 46475 and plant parts, seed, fruit, and tissue culture therefrom. The invention also provides methods for producing a pepper plant by crossing the pepper plants of the invention with themselves or another pepper plant. The invention also provides plants produced from such a crossing as well as plant parts, seed, fruit, and tissue culture therefrom.

20 Claims, No Drawings

PEPPER CULTIVAR RPP 46475 HAVING RESISTANCE TO BACTERIAL LEAF SPOT

FIELD OF THE INVENTION

This invention is in the field of pepper plants, in particular, the invention relates to novel pepper plants having resistance to bacterial leaf spot caused by *Xanthomonas*.

BACKGROUND OF THE INVENTION

Peppers are a member of the night shade family, Solanaceae, and genus *Capsicum*. They are cultivated worldwide and used as a staple in many cuisines. *Capsicum* consists of five major species, *C. annuum, C. baccatum, C. chinense, C. frutescens*, and *C. pubescens* and is commonly broken into three groups: bell peppers, sweet peppers, and hot peppers. Additionally, they are used as a source to produce dried powders (e.g. paprika). Cultivated peppers can be distinguished by their pungency, fruit shape, color, and size. Peppers can be large, blocky, thin or thick-fleshed, long, blunt-ended, heart-shaped, elongate, or slender, among other characteristics (see for example U.S. Pat. No. 6,498,287).

*Xanthomonas campestris* pv. *vesicatoria* is a gram-negative, rod-shaped bacterium that causes bacterial leaf spot (BLS) on both peppers and tomatoes. BLS is one of the most common and destructive diseases of peppers in the eastern United States. Damage from the pathogen is exhibited throughout much of the plant above ground, including leaf and fruit spots as well as stem cankers. The disease begins as water-soaked leaf spots that turn to irregular brown spots followed by yellowing. Ultimately, the leaves drop off, reducing plant productivity and allowing the potential occurrence of sunscald on the fruit. BLS also causes yield loss due to the development of raised, scab-like spots on the fruit; complete crop failure can even occur. One of the main sources of the bacterium comes from infested pepper seeds; therefore, important management practices include using disease-free seed and transplants. Pepper seed can be treated with hot water or calcium hypochlorite in order to kill the pathogen. Hot water must be used cautiously as germination can be negatively affected by high temperatures. Additional management methods, among others, include greenhouse sanitation, crop rotation, weed control, and planting resistant varieties.

Peppers represent an important and valuable crop. Thus, there is an ongoing need for improved pepper varieties having enhanced agronomic and/or consumer traits.

SUMMARY OF THE INVENTION

According to the invention, there is provided novel pepper cultivars designated P5M73, P5M84, RPP 46475, and RPP 46506. Thus, the invention also encompasses the seeds of pepper cultivars P5M73, P5M84, RPP 46475, and RPP 46506, the plants of pepper cultivars P5M73, P5M84, RPP 46475, and RPP 46506, parts of pepper cultivars P5M73, P5M84, RPP 46475, and RPP 46506 (including fruit, seed, gametes, scion, rootstock, shoots), methods of producing seed from pepper cultivars P5M73, P5M84, RPP 46475, and RPP 46506, and methods for producing a pepper plant by crossing a pepper of cultivars P5M73, P5M84, RPP 46475, and RPP 46506 with itself or another pepper plant, methods for producing a pepper plant comprising in its genetic material one or more transgenes, and the transgenic pepper plants produced by that method. The invention also relates to methods for producing other pepper plants derived from any of pepper cultivars P5M73, P5M84, RPP 46475, and RPP 46506, and pepper plants derived by the use of those methods. The present invention further relates to hybrid pepper seed and plants (and parts thereof including fruit) produced by crossing any of pepper cultivars P5M73, P5M84, RPP 46475, and RPP 46506 with another pepper plant. In general, the plants and parts thereof of the invention are diploid plants and plant parts.

In embodiments, the pepper plants or parts thereof (e.g., fruit or seed) of the invention are *Capsicum annuum* pepper plants or parts thereof. In embodiments, the pepper plants or parts thereof (e.g., fruit or seed) of the invention are sweet *Capsicum annuum* pepper plants or parts thereof, optionally producing a sweet blocky fruit.

In another aspect, the present invention provides regenerable cells for use in tissue culture of pepper cultivars P5M73, P5M84, RPP 46475, and RPP 46506. In representative embodiments, the tissue culture is capable of regenerating plants having essentially all of the physiological and morphological characteristics of the foregoing pepper plants, and of regenerating plants having substantially the same genotype as the foregoing pepper cultivars. Non-limiting examples of regenerable cells in such tissue cultures include meristematic cells, cotyledons, hypocotyl, leaves, pollen, embryos, roots, root tips, anthers, pistils, ovules, shoots, stems, petioles, pith, flowers, capsules, rootstock, scion and/or seeds as well as callus and/or protoplasts derived from any of the foregoing. Still further, the present invention provides plants regenerated from the tissue culture of the invention.

As a further aspect, the invention provides a method of producing pepper seed, the method comprising crossing a plant of pepper cultivar P5M73, P5M84, RPP 46475, or RPP 46506 with itself or a second pepper plant. P5M73, P5M84, RPP 46475, or RPP 46506 can be the female and/or male parent. Optionally, the method further comprises collecting the seed.

The invention further provides a method of producing a progeny pepper plant, the method comprising crossing a plant of pepper cultivar P5M73, P5M84, RPP 46475, or RPP 46506 with itself or a second pepper plant to produce at least a first progeny plant, which may optionally be a selfed plant or an F1 hybrid. P5M73, P5M84, RPP 46475, or RPP 46506 can be the female and/or male parent.

Another aspect of the invention provides methods for producing hybrids and other pepper plants derived from pepper cultivars P5M73, P5M84, RPP 46475, and RPP 46506356. Pepper plants derived by the use of those methods are also part of the invention as well as plant parts, (e.g., seed, gametes, fruit, scions, rootstock) and tissue culture from such hybrid or derived pepper plants.

In representative embodiments, a pepper plant derived from pepper cultivar P5M73, P5M84, RPP 46475, or RPP 46506 comprises cells comprising at least one set of chromosomes derived from pepper cultivar P5M73, P5M84, RPP 46475, or RPP 46506.

In embodiments, a pepper plant or population of pepper plants derived from pepper cultivar P5M73, P5M84, RPP 46475, or RPP 46506 comprises, on average, at least about 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from pepper cultivar P5M73, P5M84, RPP 46475, or RPP 46506, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivar P5M73, P5M84, RPP 46475, or RPP 46506, and optionally may be the result of a breeding process comprising one or two breeding crosses and one or more of selfing, backcrossing and/or double haploid techniques in any combination and any order. In embodiments, the breeding process does not include a breeding cross, and comprises selfing, backcrossing and or double haploid technology. In embodiments, the pepper plant derived from pepper cultivar P5M73, P5M84, RPP 46475, or RPP 46506 is one, two, three, four, five or more breeding crosses removed from pepper cultivar P5M73, P5M84, RPP 46475, or RPP 465066.

In embodiments, a hybrid or derived plant from pepper cultivar P5M73, P5M84, RPP 46475, or RPP 465066 comprises a desired added trait(s). In representative embodiments, a pepper plant derived from pepper cultivar P5M73, P5M84, RPP 46475, or RPP 46506 comprises some or all of the morphological and physiological characteristics of pepper cultivar P5M73, P5M84, RPP 46475, or RPP 46506 (e.g., as described in Tables 1 to 4. In embodiments, the pepper plant derived from pepper cultivar P5M73, P5M84, RPP 46475, or RPP 46506 comprises essentially all of the morphological and physiological characteristics of pepper cultivar P5M73, P5M84, RPP 46475, or RPP 46506 (e.g., as described in Tables 1 to 4), with the addition of a desired added trait(s).

The invention also relates to methods for producing a pepper plant comprising in its genetic material one or more transgenes and to the transgenic pepper plant produced by those methods. Also provided are plant parts, seed, fruit and tissue culture from such transgenic pepper plants, optionally wherein one or more cells in the plant part, seed, fruit or tissue culture comprise the transgene. The transgene can be introduced via plant transformation and/or breeding techniques.

In another aspect, the present invention provides for single locus converted plants of pepper cultivars P5M73, P5M84, RPP 46475, and RPP 46506. Plant parts, seed, fruit and tissue culture from such single locus converted plants are also contemplated by the present invention. The single transferred locus may be a dominant or recessive allele. In illustrative embodiments, the single transferred locus will confer such traits as male sterility, male fertility, herbicide resistance, pest (e.g., insect and/or nematode) resistance, modified fatty acid metabolism, modified carbohydrate metabolism, disease resistance (e.g., for bacterial, fungal and/or viral disease), male fertility, enhanced nutritional quality, increased sweetness, increased flavor, improved ripening control, improved salt tolerance, improved appearance (e.g., fruit color), industrial usage or any combination thereof. The single locus may be a naturally occurring pepper locus, a genome edited locus, a mutated locus (e.g., chemically or radiation induced), or a transgene introduced into pepper through genetic engineering techniques.

The invention further provides methods for developing pepper plants in a pepper plant breeding program using plant breeding techniques including without limitation recurrent selection, backcrossing, pedigree breeding, mutation breeding, double haploid techniques, restriction fragment length polymorphism enhanced selection, genetic marker enhanced selection, and/or transformation. Seeds, pepper plants, and parts thereof (including fruit), produced by such breeding methods are also part of the invention.

The invention also provides methods of multiplication or propagation of pepper plants of the invention, which can be accomplished using any method known in the art, for example, via vegetative propagation and/or seed.

The invention further provides a method of producing food or feed comprising (a) obtaining a pepper plant of the invention, wherein the plant has been cultivated to maturity, and (b) collecting a pepper fruit from the plant.

Additional aspects of the invention include harvested products and processed products from the pepper plants of the invention. A harvested product can be a whole plant or any plant part, as described herein. Thus, in some embodiments, a non-limiting example of a harvested product includes a seed or a fruit (immature or mature) or a part thereof), a rootstock, a scion, a shoot, a leaf, a stem, and the like.

In representative embodiments, a processed product includes, but is not limited to, cut, sliced, ground, pureed, dried, canned, jarred, packaged, frozen and/or heated fruit and/or seeds of the pepper plants of the invention, or any other part thereof. In embodiments, a processed product includes a flour, meal, sauce, salad, or puree containing a plant of the invention, or a part thereof (e.g., immature or mature fruit). In embodiments, the processed product includes washed and sliced fruit (immature or mature) or parts thereof of the invention.

Thus, the invention also provides a method of producing a processed product from a plant of the invention, the method comprising (a) obtaining a fruit of a plant of the invention; and (b) processing the fruit to produce a processed product. In embodiments, processing comprises slicing, cutting, dicing, dehydrating, pureeing, blanching and/or freezing.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of a pepper selected from pepper cultivar P5M73, P5M84, RPP 46475, or RPP 46506.

As a further aspect, the invention provides a plant of pepper cultivar P5M73, P5M84, RPP 46475, or RPP 46506.

As an additional aspect, the invention provides a pepper plant, or a part thereof, having all the physiological and morphological characteristics of a plant of pepper cultivar P5M73, P5M84, RPP 46475, or RPP 46506.

As another aspect, the invention provides fruit and/or seed of the pepper plants of the invention and a processed product from the fruit (e.g., immature or mature) and/or seed of the inventive pepper plants.

As still another aspect, the invention provides a method of producing pepper seed, the method comprising crossing a pepper plant of the invention with itself or a second pepper plant. The invention also provides seed produced by this method and plants produced by growing the seed.

As yet a further aspect, the invention provides a method for producing a seed of a pepper plant derived from pepper cultivar P5M73, P5M84, RPP 46475, or RPP 46506, the method comprising: (a) crossing a pepper plant of pepper cultivar P5M73, P5M84, RPP 46475, or RPP 46506 with a second pepper plant; and (b) allowing seed of a pepper plant derived from pepper P5M73, P5M84, RPP 46475, or RPP 46506 to form. In embodiments, the method further comprises: (c) growing a plant from the seed of step (b) to produce a plant derived from pepper cultivar P5M73, P5M84, RPP 46475, or RPP 46506; (d) selfing the plant of step (c) or crossing it to a second pepper plant to form additional pepper seed derived from pepper cultivar P5M73, P5M84, RPP 46475, or RPP 46506; and (e) optionally repeating steps (c) and (d) one or more times (e.g., one, two, one to three, one to five, one to six, one to seven, one to ten, three to five, three to six, three to seven, three to eight or three to ten times) to generate further derived pepper seed from pepper cultivar P5M73, P5M84, RPP 46475, or RPP 46506, wherein in step (c) a plant is grown from the additional pepper seed of step (d) in place of growing a plant from the seed of step (b). In embodiments, the method comprises (e) repeating steps (c) and (d) one or more times (e.g., one to three, one to five, one to six, one to seven, one to ten, three to five, three to six, three to seven, three to eight or three to ten times) to generate further derived pepper seed. As another option, in embodiments, the method comprises collecting the pepper seed. The invention also provides seed produced by these methods and plants derived from pepper cultivar P5M73, P5M84, RPP 46475, or RPP 46506 produced by growing the seed.

As another aspect, the invention provides a method of producing pepper fruit, the method comprising: (a) growing pepper cultivar P5M73, P5M84, RPP 46475, or RPP 46506; and (b) collecting fruit from the plant. The invention also provides the fruit produced by this method.

Still further, as another aspect, the invention provides a method of vegetatively propagating a plant of pepper cultivar P5M73, P5M84, RPP 46475, or RPP 46506, the method comprising: (a) collecting tissue capable of being propagated from a plant of pepper cultivar P5M73, P5M84, RPP 46475, or RPP 46506; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods.

As an additional aspect, the invention provides a method of producing a plant derived from pepper cultivar P5M73, P5M84, RPP 46475, or RPP 46506 comprising a desired added trait, the method comprising: (a) crossing a first plant of pepper cultivar P5M73, P5M84, RPP 46475, or RPP 46506 with a second pepper plant that comprises a desired trait to produce $F_1$ progeny; (b) selecting an $F_1$ progeny that comprises the desired trait; (c) crossing the selected $F_1$ progeny with the first plant of pepper P5M73, P5M84, RPP 46475, or RPP 46506 to produce backcross progeny; and (d) selecting backcross progeny comprising the desired trait to produce a plant derived from pepper P5M73, P5M84, RPP 46475, or RPP 46506 comprising a desired trait.

In embodiments, the selected progeny has resistance to races 1-10 of the bacterial leaf spot pathogen *Xanthomonas campestris* pv. *vesicatoria*. In embodiments, the selected progeny comprises all the morphological and physiological characteristics of the first plant of pepper cultivar P5M73, P5M84, RPP 46475, or RPP 46506. Optionally, the method further comprises: (e) repeating steps (c) and (d) one or more times in succession (e.g., one to five, one to six, one to seven, one to ten, three to five, three to six, three to seven, three to eight or three to ten times) to produce a plant derived from pepper cultivar P5M73, P5M84, RPP 46475, or RPP 46506 comprising a desired trait.

In representative embodiments, the invention also provides a method of producing a plant of pepper P5M73, P5M84, RPP 46475, or RPP 46506 comprising a desired added trait, the method comprising introducing a transgene conferring the desired trait into a plant of pepper P5M73, P5M84, RPP 46475, or RPP 46506. The transgene can be introduced by transformation methods (e.g., genetic engineering) or breeding techniques. Plants produced by the method and progeny thereof are also provided. In embodiments, the plant comprising the transgene has resistance to races 1-10 of the bacterial leaf spot pathogen (*Xanthomonas campestris* pv. *vesicatoria*). In embodiments, a plant comprising the transgene comprises all the morphological and physiological characteristics of pepper cultivar P5M73, P5M84, RPP 46475, or RPP 46506.

The invention also provides pepper plants produced by the methods of the invention or a selfed progeny thereof, wherein the pepper plant has the desired added trait as well as seed from such pepper plants.

According to the foregoing methods, the desired added trait can be any suitable trait known in the art including, for example, male sterility, male fertility, herbicide resistance, pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, improved appearance (e.g., fruit color) industrial usage, or any combination thereof).

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode) encodes a *Bacillus thuringiensis* endotoxin.

As a further embodiment, the invention provides a method for producing a seed of a pepper plant derived from pepper cultivars P5M73, P5M84, RPP 46475, or RPP 46506, the method comprising selfing a pepper plant of pepper cultivar P5M73, P5M84, RPP 46475, or RPP 46506 for one or more generations and allowing seed to form. Optionally, pepper cultivar P5M73, P5M84, RPP 46475, or RPP 46506 is selfed for one, two, three, four, five, six, seven, eight, nine, ten or more generations. In embodiments, P5M73, P5M84, RPP 46475, or RPP 46506 is selfed for a sufficient number of generations to produce a substantially homozygous inbred line. Also provided is pepper seed produced by the methods of the invention, optionally wherein the pepper seed grows an inbred pepper plant.

In representative embodiments, plants of the invention, including without limitation, transgenic plants, single locus converted plants, hybrid plants and pepper plants derived from pepper cultivars P5M73, P5M84, RPP 46475, and RPP 46506, are characterized, e.g., by having resistance to races 1-10 of the pathogen causing bacterial leaf spot (*Xanthomonas campestris* pv. *vesicatoria*). In representative embodiments, plants of the invention, including without limitation, transgenic plants, single locus converted plants, hybrid plants and pepper plants derived from pepper cultivars P5M73, P5M84, RPP 46475, or RPP 46506, have at least 2, 3, 4, 5, 6, 7, 8, 9, 10 or more of the morphological and physiological characteristics of pepper cultivars P5M73, P5M84, RPP 46475, or RPP 46506, respectively (e.g., as described in Tables 1 to 4), or even of all the morphological and physiological characteristics of pepper cultivars P5M73, P5M84, RPP 46475, or RPP 46506, respectively, so that said plants are not significantly different for said traits than pepper cultivar P5M73, P5M84, RPP 46475, or RPP 46506, respectively, as determined at the 5% significance level when grown in the same environmental conditions; optionally, with the presence of one or more desired additional traits (e.g., male sterility, disease resistance, pest or insect resistance, herbicide resistance, and the like).

The invention also encompasses plant parts, plant material, pollen, ovules, fruit and seed from the pepper plants of the invention. The invention also provides seeds that produce the pepper plants of the invention. Also provided is a tissue culture of regenerable cells from the pepper plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are pepper plants regenerated from a tissue culture of the invention.

In still yet another aspect, the invention provides a method of determining a genetic characteristic of pepper cultivars P5M73, P5M84, RPP 46475, or RPP 46506 or a progeny thereof using molecular genetic techniques, e.g., a method of determining a genotype of pepper cultivars P5M73, P5M84, RPP 46475, or RPP 46506 or a progeny thereof. In embodiments, the method comprises detecting in the genome of a P5M73, P5M84, RPP 46475, or RPP 46506 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

These and other aspects of the present invention are set forth in the detailed description of the invention below.

DETAILED DESCRIPTION OF THE INVENTION

The present invention is based, in part, on the development of novel pepper cultivars having desirable characteristics such as resistance to races 1-10 of the bacterial leaf spot pathogen *Xanthomonas campestris* pv. *vesicatoria*.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

I. Definitions

In the description and tables which follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of $\pm 20\%$, $\pm 10\%$, $\pm 5\%$, $\pm 1\%$, $\pm 0.5\%$, or even $\pm 0.1\%$ of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, *In re Herz*, 537 F.2d 549, 551-52, 190 U.S.P.Q. 461, 463 (CCPA 1976) (emphasis in the original); see also MPEP § 2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first-generation hybrid $F_1$ with one of the parental genotypes of the $F_1$ hybrid.

"Cotyledon". One of the first leaves of the embryo of a seed plant; typically, one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1 n chromosomes. The chromosomes in these plantlets are then induced to "double" (e.g., using chemical means) resulting in cells containing 2n chromosomes. The progeny of these plantlets is termed "double haploid" and are essentially non-segregating (e.g., are stable). The term "double haploid" is used interchangeably herein with "dihaploid."

"Essentially all the physiological and morphological characteristics". A plant having "essentially all the physiological and morphological characteristics" (and similar phrases) means a plant having all of the desired physiological and morphological characteristics of the recurrent parent, except for the characteristic(s) derived from the converted locus/loci (e.g., a single converted locus), for example, introduced via backcrossing to a pepper cultivar of the invention, a modified gene(s) resulting from genome editing techniques, an introduced transgene (i.e., introduced via genetic transformation techniques or mutation (e.g., chemical or radiation induced), when both plants are grown under the same environmental conditions. In embodiments, a plant having "essentially all of the physiological and morphological characteristics" means a plant having all of the characteristics of the reference plant with the exception of five or fewer traits, four or fewer traits, three or fewer traits, two or fewer traits, or one trait. In embodiments, the plant comprising "essentially all of the physiological and morphological characteristics of varieties P5M73, P5M84, RPP 46475, or RPP 46506 has resistance to races 1-10 of the bacterial leaf spot pathogen. In embodiments, a plant having "essentially all of the physiological and morphological characteristics" of pepper P5M73, P5M84, RPP 46475, or RPP 46506 comprises the traits of Tables 1 to 4.

"Gene". As used herein, "gene" refers to a segment of nucleic acid comprising an open reading frame. A gene can be introduced into a genome of a species, whether from a different species or from the same species, using transformation or various breeding methods.

The expression "immature harvestable stage" is understood herein to refer to a stage in the pepper fruit development where the fruit, having reached essentially full physiological development (e.g., cell division and expansion being essentially complete, fruit size and pericarp thickness having reached essentially maximum values), has not yet gone through the ripening process, e.g., are still an immature green color.

"Inbred line". As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Pepper". As used herein, the term "pepper" or "pepper plant" includes any plant classified as a *Capsicum annuum*, including *C. annuum, C. baccatum, C. chinense, C. frutescens* and *C. pubescens*. Pepper plants include varieties, cultivars and populations of *Capsicum*. In embodiments, the pepper (or part thereof, such as fruit or seed) is a *C. annuum*. Further, the pepper plants of the invention can produce pungent (hot) or sweet (mild) fruits. In embodiments, the pepper plant is a sweet pepper plant (e.g., a sweet blocky pepper plant), which typically produce immature green fruits that turn red, yellow, red, purple or brown at maturity. The fruits can have any shape including, e.g., blocky or conical. In embodiments, the fruits are blocky. Generally, plants according to the present invention are domesticated (e.g., cultivated) and produce commercially acceptable fruits (e.g., with respect to size, shape, color, yield, and the like).

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, rootstocks, scions, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, egg cells, zygotes, seeds, cuttings, cell or tissue cultures, rootstocks, scions, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing.

"Quantitative Trait Loci". Quantitative Trait Loci (QTL) refers to genetic loci that control to some degree, numerically representable traits that are usually continuously distributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A pepper plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single locus converted". A single locus converted or conversion plant refers to a plant that is developed by plant breeding techniques (e.g., backcrossing), genome editing techniques, genetic transformation techniques and/or mutation techniques (e.g., chemical or radiation induced) wherein essentially all of the desired morphological and physiological characteristics of a line are recovered in addition to the single locus introduced into the line via the plant breeding, genome editing, genetic transformation or mutation techniques.

"Substantially equivalent characteristic". A characteristic that, when compared, does not show a statistically significant difference (e.g., p=0.05) from the mean.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can encode a polypeptide or a functional non-translated RNA (e.g., RNAi).

Botanical Description of the Novel Pepper Plants of the Invention.

Pepper cultivars P5M73, P5M84, RPP 46475, and RPP 46506 are suitable for the fresh and processor markets. Cultivars P5M73, P5M84, RPP 46475 and RPP 46506 produce a compact, erect bush with a blocky, red, and shiny mature fruit. The mature fruit is also mild, sweet, and bell in shape. Additional physiological and morphological descriptions of pepper cultivars P5M73, P5M84, RPP 46475, and RPP 46506 are provided below in Tables 1-2. Tables 3-4 outline the various resistance characteristics that each hybrid and female parent possess. The hybrids both display resistance to the following: Pepper Mottle Virus, Potato Virus Y (Race 0), Tobacco Mosaic Virus (L1 gene), Tobacco Etch Virus, Tomato Spotted Wilt Virus, and races 1-10 of *Xanthomonas campestris* pv. *vesicatoria* (bacterial leaf spot). Resistance was determined through a disease resistance confirmation assay, a molecular marker assay, and the observation of a non-hypersensitive response.

To produce pepper cultivars P5M73, P5M84, RPP 46475 and RPP 46506 with resistance to BLS 1-10, a source of bs5, which confers resistance to BLS 1-10 in a non-hypersensitive manner, was utilized in the breeding process to yield pepper cultivars P5M73 and P5M84, female parents of RPP 46475 and RPP 46506, respectively. For the purposes of the present invention, the disease confirmation assay was tested against race 6; however, the presence of the bs5 marker and observation of a non-hypersensitive response indicates that pepper cultivars P5M73, P5M84, RPP 46475 and RPP 46506 are resistant to all of races 1-10.

TABLE 1

Hybrid and female parent data collected in Hobe Sound, FL and Thonotosassa, FL, respectively.

| | Hybrid (Hobe Sound) & Female Parent (Thonotosassa) | | Hybrid (Hobe Sound) & Female Parent (Thonotosassa) | |
|---|---|---|---|---|
| Trait Name | RPP46475 | P5M73 | RPP46506 | P5M84 |
| Days from transplanting until mature green: | 81 | 60 | 81 | 60 |
| Days from transplanting to mature red or yellow: | 111 | 90 | 111 | 90 |
| Days from direct seeding until mature green: | 128 | 103 | 128 | 103 |
| Days from direct seeding until mature red or yellow: | 158 | 133 | 158 | 133 |
| Plant Height (cm): | 43.6 | 35.7 | 45.7 | 36.8 |
| Plant Width (cm): | 46.5 | 35.8 | 52.2 | 35.9 |
| Length of stem from cotyledons to first flower (cm): | 18.1 | 17.1 | 19.3 | 18.8 |
| Length of third internode (cm): | 59.3 | 50.6 | 55.9 | 49.1 |
| Plant Habit: | Compact | Compact | Compact | Compact |
| Plant Attitude: | Erect | Erect | Erect | Erect |
| Basal branches: | None | None | None | None |
| Branch flexibility: | Rigid | Rigid | Rigid | Rigid |
| Stem strength: | Weak | Weak | Weak | Weak |
| Leaf width (mm): | 68.6 | 71.3 | 68.6 | 70.5 |
| Leaf length (mm): | 117.7 | 134.6 | 118.5 | 133.8 |
| Petiole length (mm): | 66.3 | 68.0 | 65.6 | 70.1 |
| Mature leaf shape: | Lanceolate | Lanceolate | Lanceolate | Lanceolate |
| Leaf & Stem pubescence: | Absent | Absent | Absent | Absent |
| Margin undulation: | Absent | Absent | Absent | Absent |
| No. flowers per axil: | 1 | 1 | 1 | 1 |
| Flower - no. of calyx lobes: | 6 | 6 | 6 | 6 |
| Flower - no. of petals: | 6 | 6 | 6 | 6 |
| Corolla Color: | White | White | White | White |
| Corolla throat markers: | Yellow (tan) | Yellow (tan) | Yellow (tan) | Yellow (tan) |
| Anther color: | Purple | Yellow | Purple | Yellow |
| Style length: | Same as stamen | Same as stamen | Same as stamen | Same as stamen |
| Self-incompatibility: | Absent | Absent | Absent | Absent |
| Fruit group: | Bell | Bell | Bell | Bell |
| Fruit: immature color: | Dark green | Dark green | Dark green | Dark green |
| Mature fruit color: | Red | Red | Red | Red |
| Fruit pungency: | Sweet | Sweet | Sweet | Sweet |
| Fruit flavor: | Mild | Mild | Mild | Mild |
| Fruit glossiness: | Shiny | Shiny | Shiny | Shiny |
| Fruit surface smoothness: | Smooth | Smooth | Smooth | Smooth |
| Fruit position: | Pendent | Pendent | Pendent | Pendent |
| Fruit calyx shape: | Saucer-shaped | Saucer-shaped | Saucer-shaped | Saucer-shaped |
| Fruit base shape: | Cupped | Cupped | Cupped | Cupped |
| Fruit apex shape: | Blunt | Blunt | Blunt | Blunt |
| Fruit longitudinal shape: | Square | Square | Square | Square |
| Fruit cross section shape: | Quadrangular | Quadrangular | Quadrangular | Quadrangular |
| Fruit set: | Concentrated | Concentrated | Concentrated | Concentrated |
| Fruit interloculary grooves: | Shallow | Shallow | Shallow | Shallow |
| Fruit pedicel shape: | Curved | Curved | Curved | Curved |

TABLE 1-continued

Hybrid and female parent data collected in Hobe Sound, FL and Thonotosassa, FL, respectively.

| Trait Name | Hybrid (Hobe Sound) & Female Parent (Thonotosassa) | | Hybrid (Hobe Sound) & Female Parent (Thonotosassa) | |
|---|---|---|---|---|
| | RPP46475 | P5M73 | RPP46506 | P5M84 |
| Fruit pedicel cavity: | Absent | Absent | Absent | Absent |
| Fruit length (mm): | 75.87 | 76.0 | 70.62 | 70.8 |
| Fruit diameter at calyx (mm): | 61.04 | 85.3 | 62.05 | 85.8 |
| Fruit diameter at mid-point (mm): | 65.45 | 93.6 | 62.51 | 92.5 |
| Fruit flesh thickness (mm): | 5.44 | 5.98 | 5.41 | 6.18 |
| Average no. fruits per plant: | 1.23 | 1.9 | 1.03 | 2.4 |
| Average fruit weight (g): | 161.06 | 193.6 | 158.01 | 165.8 |
| Average no. of locules: | 3.65 | 4.3 | 3.35 | 4.2 |

TABLE 2

Hybrid and female parent data from a second location in Parish, FL and Naples, FL, respectively.

| Trait Name | Hybrid (Parish) & Female Parent (Naples) | | Hybrid (Parish) & Female Parent (Naples) | |
|---|---|---|---|---|
| | RPP46475 | P5M73 | RPP46506 | P5M84 |
| Days from transplanting until mature green: | 81 | 60 | 81 | 60 |
| Days from transplanting to mature red or yellow: | 111 | 90 | 111 | 90 |
| Days from direct seeding until mature green: | 128 | 103 | 128 | 103 |
| Days from direct seeding until mature red or yellow: | 158 | 133 | 158 | 133 |
| Plant Height (cm): | 32.0 | 48.3 | 37.2 | 49.0 |
| Plant Width (cm): | 31.9 | 45.5 | 31.5 | 48.7 |
| Length of stem from cotyledons to first flower (cm): | 16.0 | 18.9 | 15.2 | 18.1 |
| Length of third internode (cm): | 58.4 | 39.3 | 63.5 | 45.7 |
| Plant Habit: | Compact | Compact | Compact | Compact |
| Plant Attitude: | Erect | Erect | Erect | Erect |
| Basal branches: | None | None | None | None |
| Branch flexibility: | Rigid | Rigid | Rigid | Rigid |
| Stem strength: | Weak | Weak | Weak | Weak |
| Leaf width (mm): | 83.2 | 72.7 | 67.3 | 74.0 |
| Leaf length (mm): | 141.6 | 138.7 | 110.5 | 138.3 |
| Petiole length (mm): | 63.5 | 84 | 45.1 | 96 |
| Mature leaf shape: | Lanceolate | Lanceolate | Lanceolate | Lanceolate |
| Leaf & Stem pubescence: | Absent | Absent | Absent | Absent |
| Margin undulation: | Absent | Absent | Absent | Absent |
| No. flowers per axil: | 1 | 1 | 1 | 1 |
| Flower - no. of calyx lobes: | 6 | 6 | 6 | 6 |
| Flower - no. of petals: | 6 | 6 | 6 | 6 |
| Corolla Color: | White | White | White | White |
| Corolla throat markers: | Yellow (tan) | Yellow (tan) | Yellow (tan) | Yellow (tan) |
| Anther color: | Purple | Yellow | Purple | Yellow |
| Style length: | Same as stamen | Same as stamen | Same as stamen | Same as stamen |
| Self-incompatibility: | Absent | Absent | Absent | Absent |
| Fruit group: | Bell | Bell | Bell | Bell |
| Fruit: immature color: | Dark green | Dark green | Dark green | Dark green |
| Mature fruit color: | Red | Red | Red | Red |
| Fruit pungency: | Sweet | Sweet | Sweet | Sweet |
| Fruit flavor: | Mild | Mild | Mild | Mild |
| Fruit glossiness: | Shiny | Shiny | Shiny | Shiny |
| Fruit surface smoothness: | Smooth | Smooth | Smooth | Smooth |
| Fruit position: | Pendent | Pendent | Pendent | Pendent |
| Fruit calyx shape: | Saucer-shaped | Saucer-shaped | Saucer-shaped | Saucer-shaped |
| Fruit base shape: | Cupped | Cupped | Cupped | Cupped |
| Fruit apex shape: | Blunt | Blunt | Blunt | Blunt |
| Fruit longitudinal shape: | Square | Square | Square | Square |
| Fruit cross section shape: | Quadrangular | Quadrangular | Quadrangular | Quadrangular |
| Fruit set: | Concentrated | Concentrated | Concentrated | Concentrated |
| Fruit interlocular grooves: | Shallow | Shallow | Shallow | Shallow |
| Fruit pedicel shape: | Curved | Curved | Curved | Curved |
| Fruit pedicel cavity: | Absent | Absent | Absent | Absent |
| Fruit length (mm): | 67.6 | 75.7 | 69.96 | 71.3 |

TABLE 2-continued

Hybrid and female parent data from a second location in Parish, FL and Naples, FL, respectively.

| Trait Name | Hybrid (Parish) RPP46475 | Female Parent (Naples) P5M73 | Hybrid (Parish) RPP46506 | Female Parent (Naples) P5M84 |
|---|---|---|---|---|
| Fruit diameter at calyx (mm): | 55.39 | 76.7 | 55.97 | 80.3 |
| Fruit diameter at mid-point (mm): | 58.99 | 94.1 | 62.43 | 91.9 |
| Fruit flesh thickness (mm): | 5.31 | 7.21 | 5.75 | 6.89 |
| Average no. fruits per plant: | 1.63 | 2.4 | 1.83 | 2.1 |
| Average fruit weight (g): | 123.42 | 161.3 | 147.96 | 167.1 |
| Average no. of locules: | 3.53 | 4.3 | 3.65 | 4.2 |

TABLES 3-4

Resistance summary of hybrids and female parents.

| Disease/Pathogen | RPP46475 | P5M73 | RPP46506 | P5M84 |
|---|---|---|---|---|
| Pepper Mottle Virus (PeMV) | Resistant | Susceptible | Resistant | Susceptible |
| Potato Virus Y, Race 0 (PVY0) | Resistant | Resistant | Resistant | Resistant |
| Tobacco Mosaic Virus, L1 gene (TMV(L1)) | Resistant | Resistant | Resistant | Resistant |
| Tobacco Etch Virus (TEV) | Resistant | Resistant | Resistant | Resistant |
| Tomato Spotted Wilt Virus (TSWV) | Resistant | Resistant | Resistant | Resistant |
| Xanthomonas campestris pv. vesicatoria, race 1 | Resistant | Resistant | Resistant | Resistant |
| Xanthomonas campestris pv. vesicatoria, race 2 | Resistant | Resistant | Resistant | Resistant |
| Xanthomonas campestris pv. vesicatoria, race 3 | Resistant | Resistant | Resistant | Resistant |
| Xanthomonas campestris pv. vesicatoria, race 4 | Resistant | Resistant | Resistant | Resistant |
| Xanthomonas campestris pv. vesicatoria, race 5 | Resistant | Resistant | Resistant | Resistant |
| Xanthomonas campestris pv. vesicatoria, race 6 (XCV6) | Resistant | Resistant | Resistant | Resistant |
| Xanthomonas campestris pv. vesicatoria, race 7 | Resistant | Resistant | Resistant | Resistant |
| Xanthomonas campestris pv. vesicatoria, race 8 | Resistant | Resistant | Resistant | Resistant |
| Xanthomonas campestris pv. vesicatoria, race 9 | Resistant | Resistant | Resistant | Resistant |
| Xanthomonas campestris pv. vesicatoria, race 10 | Resistant | Resistant | Resistant | Resistant |

TABLE 4

Females and hybrids, alongside various controls, were evaluated for resistance using a disease resistance confirmation assay, observation of the non-hypersensitive reaction, and the bs5 molecular marker assay.

| CROP | Cultivar | Use | PeMV | PVY0 | TMV (L1) | TEV | TSWV | XCV6 (bs5) |
|---|---|---|---|---|---|---|---|---|
| Pepper | P5M73 | Female of RPP 46475 | S | R | R | R | R | R |
| Pepper | P5M84 | Female of RPP 46506 | S | R | R | R | R | R |
| Pepper | RPP 46475 | Hybrid | R | R | R | R | R | R |
| Pepper | RPP 46506 | Hybrid | R | R | R | R | R | R |
| Pepper | Jupiter | Susceptible check (Homozygous) | S | S | R | S | S | S |
| Pepper | 9093A | Resistant check (Homozygous) | R | | | | | |
| Pepper | 5P761 | Resistant check (Homozygous) | | R | | | | |
| Pepper | Taurus | Resistant check (Homozygous) | | | | R | | |
| Pepper | 7521E | Resistant check (Homozygous) | | | | | R | |
| Pepper | Bayonet | Resistant check (Heterozygous) | | | | | R | |

TABLE 4-continued

Females and hybrids, alongside various controls, were evaluated for resistance using a disease resistance
confirmation assay, observation of the non-hypersensitive reaction, and the bs5 molecular marker assay.

| CROP | Cultivar | Use | PeMV | PVY0 | TMV (L1) | TEV | TSWV | XCV6 (bs5) |
|---|---|---|---|---|---|---|---|---|
| Pepper | ECW50R (bs5) | Resistant check (Homozygous) | | | | | | R |
| TYPE of Resistance* | | | IR | IR | HR | IR | HR | NHR |
| MARKER | | | NONE | pvr2m | TMVm | pvr2m | TSWVm | bs5m |

*IR = Intermediate resistance (not HR); HR = hypersensitive resistance; NHR = Non-hypersensitive resistance Tissue Culture.

In embodiments, pepper plants can be propagated by tissue culture and regeneration. Tissue culture of various tissues of pepper and regeneration of plants therefrom is well known and widely published. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a very high rate of success. Thus, another aspect of this invention is to provide cells which upon growth and differentiation produce pepper plants having desired characteristics of pepper cultivars P5M73, P5M84, RPP 46475, and RPP 46506 (e.g., resistance to races 1-10 of the pathogen causing bacterial leaf spot). Optionally, pepper plants can be regenerated from the tissue culture of the invention comprising all the physiological and morphological characteristics of pepper cultivars P5M73, P5M84, RPP 46475, and RPP 46506.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Additional Breeding Methods.

This invention is also directed to methods for producing a pepper plant by crossing a first parent pepper plant with a second parent pepper plant wherein the first or second parent pepper plant is a plant of pepper cultivar P5M73, P5M84, RPP 46475, or RPP 46506. Further, both first and second parent pepper plants are a plant of pepper cultivar P5M73, P5M84, RPP 46475, or RPP 46506. Thus, any of the following exemplary methods using pepper cultivar P5M73, P5M84, RPP 46475, or RPP 46506 are part of this invention: selfing, backcrosses, double haploid technology, hybrid production, crosses to populations, and the like. All plants produced using pepper cultivar P5M73, P5M84, RPP 46475, or RPP 46506 as at least one parent are within the scope of this invention, including those developed from pepper plants derived from pepper cultivar P5M73, P5M84, RPP 46475, or RPP 46506. Advantageously, pepper cultivars P5M73, P5M84, RPP 46475, and RPP 46506 can be used in crosses with other, different, pepper plants to produce first generation ($F_1$) pepper hybrid seeds and plants with desirable characteristics. The cultivars of the invention can also be used for transformation where exogenous transgenes are introduced and expressed by the cultivars of the invention. Genetic variants created either through traditional breeding methods or through transformation of the cultivars of the invention by any of a number of protocols known to those of skill in the art are intended to be within the scope of this invention.

Those skilled in the art will appreciate that peppers can be readily crossed with other peppers, e.g., another *Capsicum* including without limitation *C. annuum, C. baccatum, C. chinense, C. frutescens* or *C. pubescens*. In embodiments, the peppers of the invention are crossed with another *C. annuum*. Thus, the methods of the invention encompass crosses between pepper cultivars P5M73, P5M84, RPP 46475, and RPP 46506, and progeny and derivatives thereof, with other peppers including *C. annuum* or any other pepper type. Further, the peppers of the invention can be crossed with other sweet or hot peppers, and with peppers having any fruit shape (e.g., blocky or conical). In embodiments, the cultivars of the invention are crossed with another sweet blocky *C. annuum*.

The following describes exemplary breeding methods that may be used with pepper cultivar P5M73, P5M84, RPP 46475, and RPP 46506 in the development of further pepper plants. One such embodiment is a method for developing pepper cultivar P5M73, P5M84, RPP 46475, and RPP 46506 progeny pepper plants in a pepper plant breeding program comprising: obtaining a plant, or a part thereof, of pepper cultivar P5M73, P5M84, RPP 46475, or RPP 46506, utilizing said plant or plant part as a source of breeding material, and selecting a pepper cultivar P5M73, P5M84, RPP 46475, or RPP 46506 progeny plant with molecular markers in common with pepper cultivar P5M73, P5M84, RPP 46475, or RPP 46506 and/or with morphological and/or physiological characteristics described herein (e.g., resistance to races 1-10 of the pathogen causing bacterial leaf spot). In representative embodiments, the progeny plant has at least 2, 3, 4, 5, 6, 7, 8, 9, 10 or more of the morphological and physiological characteristics of pepper cultivars P5M73, P5M84, RPP 46475, or RPP 46506, respectively (e.g., as described in Tables 1 to 4), or even of all the morphological and physiological characteristics of pepper cultivars P5M73, P5M84, RPP 46475, or RPP 46506, respectively, so that said progeny pepper plant is not significantly different for said traits than pepper cultivar P5M73, P5M84, RPP 46475, or RPP 46506, respectively, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding, and recurrent selection. In conjunction with these steps, techniques such as RFLP-enhanced selection, genetic marker enhanced selection (for example, SNP or SSR markers), and the making of double haploids may be utilized.

Another representative method involves producing a population of pepper cultivar P5M73, P5M84, RPP 46475, or RPP 46506 progeny pepper plants, comprising crossing a pepper cultivar of the invention with another pepper plant, thereby producing a population of pepper plants, which, on average, derive 50% of their alleles from pepper cultivar P5M73, P5M84, RPP 46475, or RPP 46506, respectively. A plant of this population may be selected and repeatedly selfed or sibbed with a pepper plant resulting from these successive filial generations or backcrossed to pepper cultivar P5M73, P5M84, RPP 46475, or RPP 46506. Another approach is to make double haploid plants to achieve homozygosity. One embodiment of this invention is a pepper plant produced by these methods and that has obtained at least 50% of its alleles from pepper cultivar P5M73, P5M84, RPP 46475, or RPP 46506. In embodiments, the methods of the invention produce a population of pepper plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from pepper cultivar P5M73, P5M84, RPP 46475, or RPP 46506, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivar P5M73, P5M84, RPP 46475, or RPP 46506. One representative embodiment of this invention is the pepper plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from pepper cultivar P5M73, P5M84, RPP 46475, or RPP 46506, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and/or double haploid technology.

One of ordinary skill in the art of plant breeding would know how to evaluate the traits of two plant varieties to determine if there is no significant difference between the two traits expressed by those varieties. For example, see Fehr and Walt, Principles of Cultivar Development, pp. 261-286 (1987). Thus, the invention includes pepper cultivar P5M73, P5M84, RPP 46475, and RPP 46506 progeny pepper plants characterized by having resistance to races 1-10 of the bacterial leaf spot pathogen. In embodiments, the invention encompasses progeny plants having a combination of at least 2, 3, 4, 5 or 6 characteristics as described herein for pepper cultivar P5M73, P5M84, RPP 46475, or RPP 46506, so that said progeny pepper plant is not significantly different for said traits than pepper cultivar P5M73, P5M84, RPP 46475, or RPP 46506, respectively, as determined at the 5% significance level when grown in the same environmental conditions. Using techniques described herein and those known in the art, molecular markers may be used to identify said progeny plant as progeny of pepper cultivar P5M73, P5M84, RPP 46475, and RPP 46506. Mean trait values may be used to determine whether trait differences are significant, and optionally the traits are measured on plants grown under the same environmental conditions.

Progeny of pepper cultivar P5M73, P5M84, RPP 46475, and RPP 46506 may also be characterized through their filial relationship with pepper cultivar P5M73, P5M84, RPP 46475, and RPP 46506, respectively, as for example, being within a certain number of breeding crosses of pepper cultivar P5M73, P5M84, RPP 46475, and RPP 46506. A breeding cross is a cross made to introduce new genetics into the progeny, and is distinguished from a cross, such as a self or a sib cross, made to select among existing genetic alleles. The lower the number of breeding crosses in the pedigree, the closer the relationship between pepper cultivars P5M73, P5M84, RPP 46475, or RPP 46506 and its progeny. For example, progeny produced by the methods described herein may be within 1, 2, 3, 4, 5 or more breeding crosses of pepper cultivars P5M73, P5M84, RPP 46475, or RPP 46506.

In representative embodiments, a pepper plant derived from pepper cultivars P5M73, P5M84, RPP 46475, or RPP 46506 comprises cells comprising at least one set of chromosomes derived from pepper cultivars P5M73, P5M84, RPP 46475, or RPP 46506.

In embodiments, the pepper plant or population of pepper plants derived from pepper cultivars P5M73, P5M84, RPP 46475, or RPP 46506 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from pepper cultivars P5M73, P5M84, RPP 46475, or RPP 46506, e.g., at least 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of pepper cultivars P5M73, P5M84, RPP 46475, or RPP 46506, and optionally may be the result of one or more of selfing, sibbing, backcrossing and/or double haploid techniques in any combination and any order. In embodiments, the breeding process does not include a breeding cross, and comprises selfing, backcrossing and/or double haploid technology.

In embodiments, the pepper plant derived from pepper cultivars P5M73, P5M84, RPP 46475, or RPP 46506 is one, two, three, four, five or more breeding crosses removed from pepper cultivars P5M73, P5M84, RPP 46475, or RPP 46506. In embodiments, the pepper plant derived from pepper cultivars P5M73, P5M84, RPP 46475, or RPP 46506 is two or less, three or less, four or less, or five or less breeding crosses removed from pepper cultivars P5M73, P5M84, RPP 46475, or RPP 46506.

In representative embodiments, a plant derived from pepper cultivars P5M73, P5M84, RPP 46475, or RPP 46506 is a double haploid plant, a hybrid plant or an inbred plant.

In embodiments, a hybrid or derived plant from pepper cultivars P5M73, P5M84, RPP 46475, or RPP 46506 comprises a desired added trait. In representative embodiments, a pepper plant derived from pepper cultivars P5M73, P5M84, RPP 46475, or RPP 46506 comprises all of the morphological and physiological characteristics of pepper cultivars P5M73, P5M84, RPP 46475, or RPP 46506 (e.g., as described herein, in particular, in Tables 1 to 4). In embodiments, the pepper plant derived from pepper cultivars P5M73, P5M84, RPP 46475, or RPP 46506 comprises all or essentially all of the morphological and physiological characteristics of pepper cultivars P5M73, P5M84, RPP 46475, or RPP 46506 (e.g., as described herein, in particular, in Tables 1 to 4), with the addition of a desired added trait.

Genetic Transformation.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species, the same species or an artificial sequence, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of pepper plants disclosed herein.

Genetic engineering techniques can be used (alone or in combination with breeding methods) to introduce one or more desired added traits into plant, for example, pepper cultivars P5M73, P5M84, RPP 46475, or RPP 46506 or progeny or pepper plants derived thereof. Once a transgene has been introduction into a plant by genetic transformation, it can be transferred to other plants via conventional breeding.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid and can be used alone or in combination with other plasmids, to provide transformed pepper plants using transformation methods as described herein to incorporate transgenes into the genetic material of the pepper plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

Commonly used selectable markers in plants include, but are not limited to: neomycin phosphotransferase II (nptII) conferring resistance to kanamycin, hygromycin phosphotransferase conferring resistance to the antibiotic hygromycin, bacterial selectable markers that confer resistance to antibiotics (e.g., gentamycin acetyl transferase, streptomycin phosphotransferase, and aminoglycoside-3'-adenyl transferase, selectable markers conferring resistance to herbicides (e.g., glyphosate, glufosinate, or bromoxynil). Selection of transformed plant cells can also be based on screening presumptively transformed plant cells rather than direct genetic selection of transformed cells for resistance to a toxic substance such as an antibiotic; such markers include without limitation alpha-glucuronidase (GUS), alpha-galactosidase, luciferase, and Green Fluorescent Protein (GFP) and mutant GFPs.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

Many suitable promoters are known in the art and can be selected and used to achieve the desired outcome.

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981). According to a representative embodiment, the transgenic plant provided for commercial production of foreign protein is a pepper plant of the invention. In another embodiment, the biomass of interest is seed and/or fruit.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those transgenes that confer resistance to confer resistance to plant pests (e.g., nematode or insect) or disease (e.g., fungal, bacterial or viral), transgenes that confer herbicide tolerance, transgenes that confer male sterility, and transgenes that confer or contribute to a value-added trait such as increased nutrient content (e.g., iron, nitrate), increased sweetness (e.g., by introducing a transgene coding for monellin), modified fatty acid metabolism (for example, by introducing into a plant an antisense sequence directed against stearyl-ACP desaturase to increase stearic acid content of the plant), modified carbohydrate composition (e.g., by introducing into plants a transgene coding for an enzyme that alters the branching pattern of starch), modified fruit color (e.g., external fruit color), or modified flavor profile of the fruit.

In embodiments, the transgene encodes a non-translated RNA (e.g., RNAi) that is expressed to produce targeted inhibition of gene expression, thereby conferring the desired trait on the plant.

In embodiments, the transgene encodes the machinery used for genome editing techniques.

Any transgene, including those exemplified above, can be introduced into the pepper plants of the invention through a variety of means including, but not limited to, transformation (e.g., genetic engineering techniques), conventional breeding, and introgression methods to introduce the transgene into other genetic backgrounds.

Methods for Plant Transformation.

Numerous methods for plant transformation have been developed, including biological and physical plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993). Commonly used plant transformation methods include *agrobacterium*-mediated transformation and direct transgene transfer methods (e.g., microprojectile-mediated transformation, sonication, liposome or spheroplast fusion, and electroporation of protoplasts or whole cells).

Following transformation of plant target tissues, expression of selectable marker transgenes (e.g., as described above) allows for preferential selection of transformed cells, tissues and/or plants, using regeneration and selection methods now well known in the art.

The foregoing methods for transformation are typically used to produce a transgenic pepper line. The transgenic pepper line can then be crossed with another (non-transgenic or transgenic) line in order to produce a new transgenic pepper line. Alternatively, a transgene that has been engineered into a particular plant using transformation techniques can be introduced into another plant or line using traditional breeding (e.g., backcrossing) techniques that are well known in the plant breeding arts. For example, a backcrossing approach can be used to move an engineered transgene from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Locus Conversion.

When the term "plant" is used in the context of the present invention, this term also includes any locus conversions of that plant or variety. The term "locus converted plant" as used herein refers to those plants that are developed, for example, by backcrossing, genome editing, genetic transformation and/or mutation, wherein essentially all of the desired morphological and physiological characteristics of a variety (e.g., resistance to races 1-10 of the pathogen causing bacterial leaf spot) are recovered in addition to the one or more genes introduced into the variety. To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene/locus for the desired characteristic is termed the "nonrecurrent" or "donor parent." This terminology refers to the fact that the nonrecurrent parent is generally used one time in the breeding e.g., backcross) protocol and therefore does not recur. The gene/locus that is transferred can be a native gene/locus, a mutated native gene/locus or a transgene introduced by genetic engineering techniques into the plant (or ancestor thereof). The parental plant into which the locus/loci from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the locus/loci of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred locus/loci and associated trait(s) from the nonrecurrent parent.

Genetic Analysis of Pepper Cultivars P5M73, P5M84, RPP 46475, and RPP 46506.

The invention further provides a method of determining a genetic characteristic of pepper cultivars P5M73, P5M84, RPP 46475, and RPP 46506 or a progeny thereof, e.g., a method of determining a genotype of pepper cultivars P5M73, P5M84, RPP 46475, or RPP 46506 or a progeny thereof. In embodiments, the method comprises detecting in the genome of a P5M73, P5M84, RPP 46475, or RPP 46506 plant, or a progeny plant thereof, at least a first polymorphism, e.g., by detecting a nucleic acid marker by a method comprising nucleic acid amplification and/or nucleic acid sequencing. To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

DEPOSIT

Applicants have made a deposit of at least 625 seeds of pepper cultivar RPP 46475 with the American Type Culture Collection (ATCC), 10801 University Boulevard, Manassas, Va., 20110-2209 U.S.A. under ATCC Deposit Nos. PTA-127139. These deposits will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§ 1.801-1.809, including providing an indication of the viability of the samples. During the pendency of this application, access to the deposited material will be afforded to the Commissioner on request. All restrictions on the availability of the deposited material from the ATCC to the public will be irrevocably removed upon granting of the patent. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC § 2321 et seq.).

Access to these deposits will be available during the pendency of this application to persons determined by the Commissioner of Patents and Trademarks to be entitled thereto under 37 C.F.R. § 1.14 and 35 U.S.C. § 122. Upon allowance of any claims in this application directed to a variety, all restrictions on the availability to the public of that variety will be irrevocably removed by affording access to a deposit of at least 2500 seeds of the same variety with the American Type Culture Collection, 10801 University Boulevard, Manassas, Va. 20110-2209 U.S.A.

What is claimed is:

1. A seed of a pepper selected from pepper cultivar RPP 46475 a representative sample of seed having been deposited under ATCC Accession No. PTA-127139.

2. A plant of pepper cultivar RPP 46475 grown from the seed of claim 1.

3. A pepper plant having all the physiological and morphological characteristics of the pepper plant of claim 2.

4. A seed that produces the plant of claim 3.

5. A plant part of the pepper plant of claim 2, wherein the plant part is a fruit, a scion, a rootstock, a shoot, an anther, pollen, an ovule, a root, a leaf, or a cell.

6. A tissue culture of regenerable cells of the plant of claim 2.

7. A pepper plant regenerated from a tissue culture of regenerable cells of the plant of claim 2, wherein the regenerated pepper plant comprises all of the physiological and morphological characteristics of the plant of claim 2.

8. A method of producing pepper seed, the method comprising crossing the plant of claim 2 with itself or a second pepper plant and harvesting the resulting seed.

9. A method of developing a pepper line in a pepper plant breeding program using plant breeding techniques, which include employing a pepper plant, or its parts, as a source of plant breeding material, the method comprising:
   (a) obtaining the pepper plant, or parts thereof, of claim 2 as a source of breeding material; and
   (b) applying plant breeding techniques.

10. A method for producing a seed of a pepper plant derived from the plant of claim 2, the method comprising:
   (a) crossing a pepper plant of pepper cultivar RPP 46475 with a second pepper plant;
   (b) allowing seed to form;
   (c) growing a plant from the seed of step (b) to produce a plant derived from pepper cultivar RPP 46475;
   (d) selfing the plant of step (c) or crossing it to a second pepper plant to form additional pepper seed derived from pepper cultivar RPP 46475; and
   (e) optionally repeating steps (c) and (d) one or more times to generate further derived pepper seed from pepper cultivar RPP 46475, wherein in step (c) a plant is grown from the additional pepper seed of step (d) in place of growing a plant from the seed of step (b).

11. A method of producing pepper fruit, the method comprising:
   (a) growing the plant of claim 2 to produce a pepper fruit; and
   (b) harvesting the pepper fruit from the plant.

12. A method of vegetatively propagating the plant of claim 2, the method comprising:
   (a) collecting tissue capable of being propagated from a plant of pepper cultivar RPP 46475;
   (b) cultivating the tissue to obtain proliferated shoots; and
   (c) rooting the proliferated shoots to obtain rooted plantlets.

13. The method of claim 12, further comprising growing plants from the rooted plantlets.

14. A plant obtained by the method of claim 13, wherein the plant comprises all of the morphological and physiological characteristics of pepper cultivar RPP 46475.

15. A method of producing a plant of pepper cultivar RPP 46506 comprising a desired added desired trait, the method comprising introducing a transgene conferring the desired trait into the plant of claim 2.

16. A pepper plant produced by the method of claim 15, wherein the pepper plant is a transformed pepper plant comprising the desired added trait and otherwise all of the morphological and physiological characteristics of pepper cultivar RPP 46475.

17. A seed that produces the plant of claim 16,
   wherein the seed produces a transformed plant of RPP 46475 that has the desired trait and otherwise all of the morphological and physiological characteristics of pepper cultivar RPP 46475.

18. A method for producing a pepper seed, the method comprising selfing the plant of claim 2, which is pepper cultivar RPP 46475, for one or more generations and allowing seed to form.

19. A method of determining a genotype of pepper cultivar RPP 46475, the method comprising:
(a) obtaining a sample of nucleic acids from the plant of claim 2; and
(b) detecting a polymorphism in the nucleic acid sample using molecular biology techniques, thereby determining the genotype of pepper cultivar RPP 46475.

20. A plant or plant part of pepper cultivar RPP 46475, a representative sample of seed having been deposited under ATCC Accession No. PTA-127139, or a seed that produces pepper cultivar RPP 46475.

\* \* \* \* \*